United States Patent [19]

Kuemmerle et al.

[11] Patent Number: 5,227,311
[45] Date of Patent: Jul. 13, 1993

[54] INTRINSIC FACTOR TO DETERMINE B12

[75] Inventors: Steven C. Kuemmerle, Grayslake; Gary L. Boltinghouse, Jr., McHenry; Billy J. Green, Vernon Hills, all of Ill.

[73] Assignee: Abbott Laboratories, Abbott Park, Ill.

[21] Appl. No.: 773,388

[22] Filed: Oct. 8, 1991

Related U.S. Application Data

[63] Continuation-in-part of Ser. No. 534,381, Jun. 6, 1990, Pat. No. 5,104,815, which is a continuation-in-part of Ser. No. 255,682, Oct. 11, 1988, abandoned.

[51] Int. Cl.$^5$ .................. G01N 33/566; G01N 33/567
[52] U.S. Cl. ..................... 436/501; 436/503; 436/505; 436/76; 435/4; 435/21
[58] Field of Search ............... 436/505, 76, 501, 503; 435/4, 21

[56] References Cited

U.S. PATENT DOCUMENTS 3,505,019 4/1970 Axen et al. ................... 436/505

Primary Examiner—Sam Rosen
Attorney, Agent, or Firm—Richard D. Schmidt

[57] ABSTRACT

A method for purifying an aqueous intrinsic factor solution which contains R-protein is disclosed. The method involves adding to the intrinsic factor solution an amount of colloidal silica to disperse lipid emulsion, an amount of cobinamide sufficient to bind substantially all of the R-protein in the solution and an amount of an intrinsic factor affinity resin sufficient to bind the intrinsic factor in the solution, washing the bound cobinamide and the R-protein from the resin, eluting the intrinsic factor from the resin, and dialyzing the eluted intrinsic factor. The purified intrinsic factor possesses less than 0.004 percent cross reactivity with cobinamides, and at least 95 percent of the proteins in the purified material can bind cobalamins. A conjugate of microparticles and the purified intrinsic factor is also disclosed, as is a kit for conducting an assay for cobalamins which includes a conjugate of microparticles and purified intrinsic factor. A method for conducting an assay for cobalamins, which method involves the use of a conjugate of microparticles and purified intrinsic factor is also disclosed.

6 Claims, 8 Drawing Sheets

INTRINSIC FACTOR TO DETERMINE B12

RELATED APPLICATIONS

This is a continuation-in-part of co-pending application U.S. Ser. No. 07/534,381 filed on Jun. 6, 1990, now U.S. Pat. No. 5,104,815 issued Apr. 14, 1992 which is a continuation-in-part of U.S. Ser. No. 07/255,682 filed on Oct. 11, 1988, now abandoned.

FIELD OF THE INVENTION

This invention relates to the purification of intrinsic factor, to the purified intrinsic factor, to conjugates which include the purified intrinsic factor and are useful in conducting assays for B12, to a method for determining B12 which involves use of the purified intrinsic factor, and to a kit which includes the purified intrinsic factor and is useful for determining B12.

BACKGROUND OF THE INVENTION

The following discussion of competitive protein binding assays (CPBA) and definitions of terms often used with respect to CPBAs are set forth herein as background to facilitate the understanding of the disclosure and claims hereof.

The term "analyte" refers to the molecule, which may be, but is not necessarily, vitamin 12, to be detected.

The term "test sample" typically refers to a sample of body fluid such as plasma, serum, ascites, lymphatic fluids, cerebral spinal fluid, nipple fluid discharge, urine and other body fluids that may contain the analyte of interest. Optionally, the test sample can be diluted in a suitable diluent buffer, such as phosphate buffered saline with serum components, to provide a sample volume that is required by the particular CPBA.

The term "specific binding member" refers to a member of a specific binding pair, i.e., two different molecules wherein one of the molecules through chemical or physical means specifically binds to the second molecule. In addition to antigen and antibody specific binding pairs such as the allergen and antibody pair, other specific binding pairs include vitamin B12 and intrinsic factor, vitamin B12 and R-protein, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence protein, polymeric acids and bases, dyes and protein binders, peptides and specific protein binders (e.g., ribonuclease, S-peptide and ribonuclease S-protein), and the like. Furthermore, specific binding pairs can include members that are analogs of the original specific binding member, for example the cyanocobalamin analog, cobinamide, may bind R-protein. If the specific binding member is an immunoreactant it can be, for example, an antibody, antigen, hapten, or complex thereof. If an antibody is used, it can be a monoclonal or polyclonal antibody, a recombinant protein or antibody, a mixture or mixtures or a fragment or fragments thereof, as well as a mixture of an antibody and other specific binding members. The details of the preparation of such antibodies and their suitability for use as specific binding members are well-known to those skilled-in-the-art.

The term "indicator reagent" refers to an assay reagent comprising a detectable label directly or indirectly attached to a specific binding member which is capable of directly or indirectly binding to the analyte and thereby indicating the presence, absence or amount of the analyte in a test sample. A variety of different indicator reagents can be formed by varying either the label or the specific binding member. In general, the indicator reagent is detected after it has formed a complex with either the analyte or a complementary specific binding member, but the unbound indicator reagent can also be detected.

The term "label" refers to any substance which is attached to a specific binding member and which is capable of producing a signal that is detectable by visual or instrumental means. Labels can include chromogens; catalysts; fluorescent compounds; chemiluminescent compounds; radioactive isotopes; direct visual labels including colloidal metallic and non-metallic particles, dye particles, enzymes or substrates, or organic polymer latex particles; liposomes or other vesicles containing signal producing substances; and the like.

Many enzymes suitable for use as labels are disclosed in U.S. Pat. No. 4,275,149, columns 19–23, herein incorporated by reference. For example, an enzyme/substrate signal producing system useful with 4-methylumbilliferyl phosphate is the enzyme alkaline phosphatase. If horseradish peroxidase is used, o-Phenylenediamine can be added as an enzyme substrate to form a colored product which can be detected and/or measured visually or instrumentally.

In an alternative signal producing system, the label can be a fluorescent compound where no enzymatic manipulation of the label is required to produce a detectable signal. Fluorescent molecules such as fluorescein, coumarin, phycobiliprotein, rhodamine and their derivatives and analogs are suitable for use as labels in this system.

Another class of labels includes the visually detectable, colored particles which enable a direct colored readout of the presence or concentration of the analyte in the test sample without the need for using additional signal producing reagents. Materials for use as such particles include colloidal metals, such as gold, and dye particles as disclosed in U.S. Pat. Nos. 4,313,734 and 4,373,932. The preparation and use of non-metallic colloids, such as colloidal selenium particles, are disclosed in co-owned and copending U.S. patent application Ser. No. 072,084, filed Jul. 9, 1987, which is incorporated by reference herein. Organic polymer latex particles for use as labels are disclosed in co-owned and copending U.S. patent application Ser. No. 248,858, filed Sep. 23, 1988, which is incorporated by reference herein. The selection of a particular label is not critical, so long as the label is capable of generating a detectable signal either by itself or in conjunction with one or more additional signal producing substances.

The term "signal producing component" refers to any substance capable of reacting with another assay reagent or the analyte to produce a reaction product or signal that indicates the presence of the analyte and that is detectable by visual or instrumental means. "Signal production system", as used herein, refers to the group of assay reagents that are needed to produce the desired reaction product or signal. For example, one or more signal producing components can be used to react with a label and generate the detectable signal, i.e., when the label is an enzyme, amplification of the detectable signal is obtained by reacting the enzyme with one or more substrates or additional enzymes to produce a detectable reaction product.

The term "capture binding member" refers to a specific binding member which can bind directly or indirectly to the analyte or indicator reagent and which is bound or is capable of being bound to a solid phase, or is capable of being precipitated, such that the capture binding member can be separated from the test sample and other assay reagents.

The term "capture reagent" refers to a capture binding member which is directly or indirectly attached to a solid phase material to enable the separation of the capture binding member, and analyte or indicator reagent that is bound thereto, from unbound analyte and assay reagents. Typically, the attachment of the capture binding member to the solid phase material is substantially irreversible and can include covalent mechanisms. A capture reagent in which a capture binding member is indirectly attached to a solid phase can be produced by reacting a coupling agent of the instant invention with both the solid phase material and the capture reagent; the product of such a reaction is an example of a ,conjugate, In an agglutination assay, the capture binding member of the capture reagent can be bound to a soluble carrier material such as bovine serum albumin.

Once complex formation occurs between the assay components, the solid phase can be used as a separation mechanism. For example, the reaction mixture can be contacted with the solid phase material, and the solid phase material retains the newly formed reaction complex(es). Alternative methods can be used to perform this separation step, such as using a solid phase which itself binds to the capture binding member; affixing to the solid phase a binding member that is specific for the capture binding member; or affixing to the solid phase a reactive agent, such as a charged substance, which will attract and bind an oppositely charged substance that has been bound to the capture binding member, as disclosed in co-owned and copending U.S. patent application Ser. No. 150,278, filed Jan. 29, 1988, which is incorporated by reference herein. Either the binding member that is specific for the capture binding member or the reactive agent (e.g., a charged substance) can be bound to or chemically reacted with a coupling agent according to the invention which is also bound to or chemically reacted with the solid phase material; these are also examples of conjugates.

Assay devices can have many configurations, several of which are dependent upon the material chosen for the solid phase. The term "solid phase material" refers to any suitable chromatographic, bibulous, porous or capillary material or other conventional solid material, well-known to those skilled-in-the-art for use in immobilizing specific binding members. Solid phase materials can include a fiberglass, cellulose or nylon pad for use in a flow-through assay device having one or more layers containing one or more of the assay reagents; a dipstick for a dip and read assay; a test strip for chromatographic (e.g., paper or glass fiber) or thin layer chromatographic (e.g., nitrocellulose) techniques in which one or all of the reagents are contained in separate zones of a single strip of solid phase material; or an absorbent material well known to those skilled-in-the-art. The solid phase material can also include, without limitation, polyacrylamide or polystyrene beads, microparticles or tubes and maybe magnetic or not, a microtitre plate with one or more reaction wells, a microparticute material as known in the art or a glass or plastic test tube.

Natural, synthetic or naturally occurring materials that are synthetically modified, can be used as a solid phase material including polysaccharides, e.g., cellulose materials including paper, cellulose and cellulose derivatives such as cellulose acetate, nitrocellulose and cellulose acetate/nitrate; silica; fiberglass; inorganic materials such a deactivated alumina, diatomaceous earth or other inorganic finely divided material uniformly dispersed in a porous polymer matrix, with polymers such as vinyl chloride, vinyl chloride-propylene copolymer, and vinyl chloridevinyl acetate copolymer; cloth, both naturally occurring (e.g., cotton) and synthetic (e.g., nylon); porous gels such as silica gel, agarose, dextran and gelatin; polymeric films such as polyacrylamide; magnetic particles; microtitre plates; polystyrene tubes; protein binding membranes; Sephadex (Pharmacia Fine Chemicals, Inc., Piscataway, N.J.); Trisacryl (Pointet-Girard, France); silicon particles; porous fibrous matrixes; and the like. The solid phase material should have a reasonable inherent strength or strength can be provided by means of a support, and it should not interfere with the production of a detectable signal.

When the specific binding member of the capture reagent is affixed to microparticles, those particles can be retained in a column, suspended in a mixture of soluble reagents and test sample, or retained and immobilized by another solid phase base material. By "retained and immobilized" is meant that the particles, associated with the solid phase base material, are not capable of substantial movement to positions elsewhere within that material. The size of the particles is not critical, although it is preferred that the average diameter be smaller than the average pore size of the solid phase base material if such is used, and they must be of such a size that they can be suspended in a suitable liquid if they are to be used in an agglutination assay.

The term "ancillary specific binding member" refers to a specific binding member used in addition to the capture binding member and the indicator reagent which becomes a part of the detectable binding complex. One or more ancillary specific binding members can be used in an assay. For example, an ancillary specific binding member can be used in an assay where the capture binding member is capable of binding the ancillary specific binding member which is in turn capable of binding the solid phase.

It will be appreciated by those skilled-in-the-art that the selection of any given label, ancillary binding member or solid phase material is generally not critical to the present invention. The materials are chosen to optimize the results provided by the chosen assay configuration.

The use of insolubilized 3,3'-diaminodipropylamine to purify intrinsic factor and transcobalamin I by biospecific affinity chromatology, has been suggested, *Biochim, Biophys. Acta,* 379(1) 1890192 (1875). Cobalamin was attached through a temp.-labile linkage to the insolubilized 3,3'-diaminodipropylamine. Desorption yielded the intrinsic factor or the transcobalamin in solution saturated with cobalamin. U.S. Pat. No. 3,591,678 discloses a similar process where a diethylaminoethyl cellulose resin is brought into contact with a solution of impure intrinsic factor to adsorb the intrinsic factor on the resin, the resin is filtered from the solution, the intrinsic factor is eluted from the resin with a buffer solution, and the purified intrinsic factor is recovered from the eluate as a residue. U.S. Pat. No. 3,591,678, granted Jul. 6, 1971 to Ellenbogen et al., also discloses the use of a diethylaminoethyl cellulose resin to purify intrinsic factor and the use of a buffer solution to elute the intrinsic factor.

UK patent 900459, according to the record in World Patent Index Accession No.: 6603585F/00, discloses a method for producing an improved "Castle's intrinsic factor concentrate" from desiccated and defatted hog pyloric or stomach mucosa. The method involves treating with sodium chloride to produce a precipitate, separating the liquor, adjusting the pH of the liquor to about 9, adjusting the pH of the liquor to about 1.5, removing precipitate formed, adjusting the pH of the supernatant to about 4.5, and making seven successive additions of solid ammonium sulfate; precipitate formed after each ammonium sulfate addition is separated from the liquor, mixed with water and dialyzed, and intrinsic factor concentrate is recovered from each, e.g., by freeze drying. UK patent 951,984 also discloses a method which involves several purification steps followed by precipitation of intrinsic factor with ammonium sulfate (sodium sulfate is also said to be operable).

Cobalamins have the general structure shown in FIG. 1 of the attached drawings. While cobalamins have sometimes been referred to as vitamin B12, there are actually several different types of cobalamins which differ from each other by the R substituent shown in the FIG. 1 structure: cyanocobalamin(R=cyano), hydroxycobalamin(R=hydroxy), aquacobalamin(R=H20), nitrocobalamin (R=NO₂), 5'deoxyadenosylcobalamin (R=5'deoxyadenosyl), and methylcobalamin (R=methyl). Each of these cobalamins is considered generally to be a vitamin B12: cyanocobalamin (vitamin B12), hydroxycobalamin (vitamin B12a), aquacobalamin (vitamin B12b), nitrocobalamin (vitamin B12c), 5'deoxyadenosylcobalamin (coenzyme B12), methylcobalamin (methyl B12). The various cobalamins have similar metabolic activity. Cyanocobalamin, however, is more stable than the others. The cobalamins are involved in many metabolic functions and are essential for normal growth and nutrition, hematopoiesis, production of all epithelial cells, and maintenance of myelin throughout the nervous system.

In addition to the physiologically-active cobalamins discussed above, there are also physiologically inactive vitamin B12 analogues present in human biological fluids. These analogues can be present in amounts equal to, or exceeding, the levels of vitamin B12. An example of physiologically inactive analogue of vitamin B12 is cobinamide dicyanide.

A deficiency in vitamin B12 manifests itself in ineffective hematopoiesis, inadequate myelin synthesis, inadequate maintenance of the epithelial cells of the alimentary tract, and generalized anemia. However, except for inadequate myelin synthesis, these symptoms are common to many megaloblastic anemias, regardless of cause.

To pinpoint the cause of such anemias, it is necessary to test for vitamin B12 deficiencies. There are a variety of different assays for vitamin B12: colorimetric, spectroscopic, fluorometric and radioactive isotope. The most common employs a cobalt 57 radioactive isotope in lieu of the cobalt in the corrin nucleus of the vitamin B12 molecule. The radioactively labelled molecule and B12 intrinsic factor are added to a sample containing B12, and the radioactively labelled B12 and the B12 in the sample compete for binding sites on B12 intrinsic factor. The B12 intrinsic factor is associated with a solid phase, so the amount of radioactivity on the solid phase or in the sample will be proportional to the amount of B12 in the original sample.

Physiologically-inactive vitamin B12 analogues normally present in human serum, have been shown to cause interferences in assays that employ cobalamin binders other than intrinsic factor, or intrinsic factor of low purity. These non-intrinsic factor vitamin B12 binding proteins are collectively termed R-proteins. R-proteins bind vitamin B12, and physiologically-inactive B12 analogues with equal affinity, where as intrinsic factor binds vitamin B12 to the virtual exclusion of the inactive analogues. It is essential therefore, that methods used to assay for vitamin B12 in human biological fluids employ high purity intrinsic factor as capture binding member in order to avoid interference due to inactive B12 analogues.

SUMMARY OF THE PRESENT INVENTION

Figure 1:
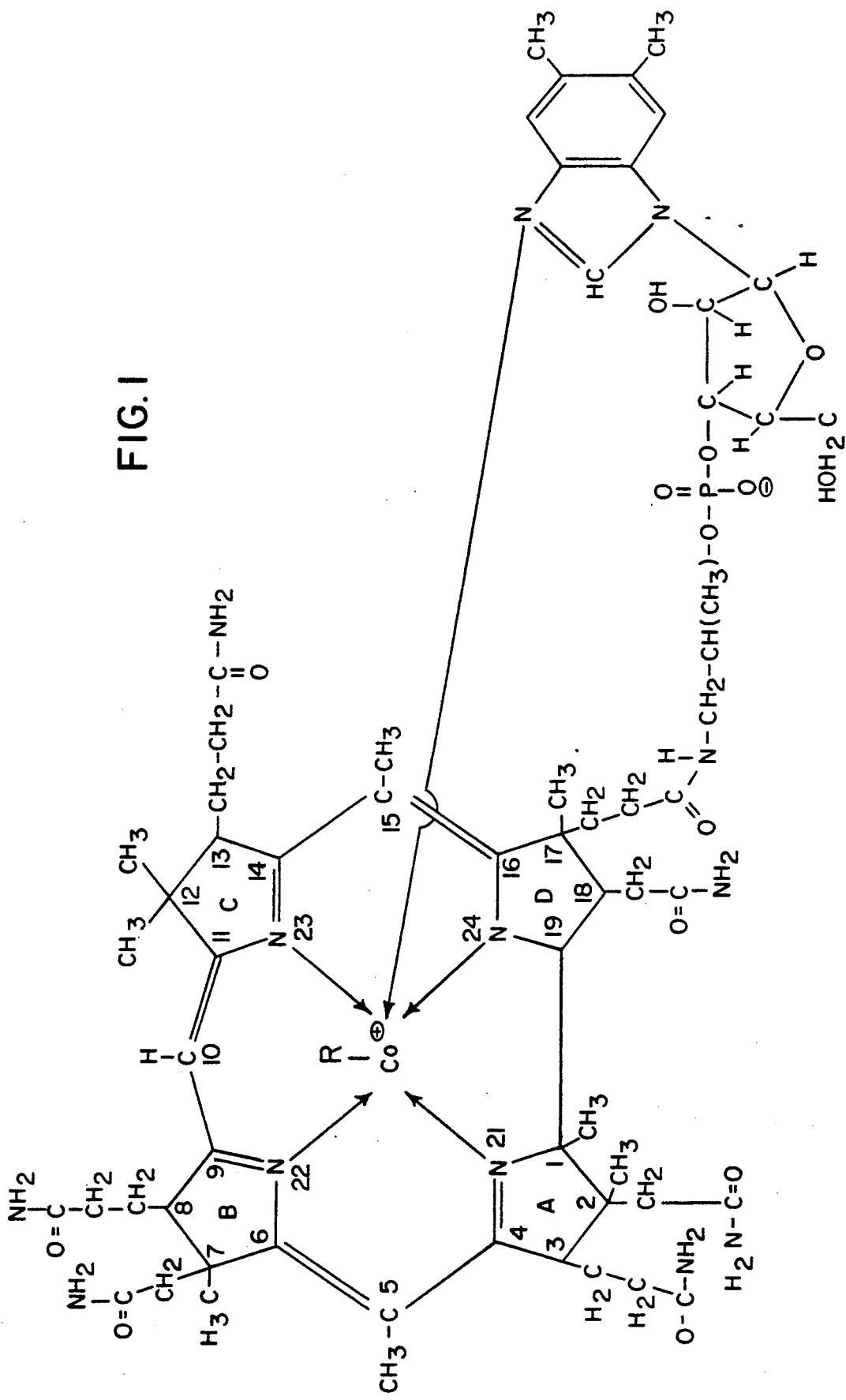
FIG. 1 is a formula showing the general structure of cobalamins.

The instant invention is based upon the discovery of a method for producing purified intrinsic factor employing cobinamide and colloidal silica, and the further discovery that a conjugate of the purified intrinsic factor with microparticles is unexpectedly useful in carrying out an enzyme immunoassay for cobalamins, making the assay substantially more sensitive and specific for vitamin B12 than when an otherwise identical conjugate of the purified intrinsic factor from which R-proteins have not been removed is used in the assay.

The prior art purification methods discussed previously are not stringent enough to provide an intrinsic factor preparation free of contaminating R-protein. The use of the cyanocobalamin analogue, cobinamide, in conjunction with colloidal silica, allows for the production of intrinsic factor of high purity, as discussed in Example 1 in the "Description of the Preferred Embodiments" section that follows.

DESCRIPTION OF THE PREFERRED EMBODIMENTS

The invention will be more fully understood from the following examples, which constitute the best modes presently contemplated by the inventors. It is to be understood, however, that the examples are presented solely for the purpose of illustration, and are not to be construed as limiting.

As used herein, and in the appended claims, the terms "percent" and "parts" refer to percent and parts by weight, unless otherwise indicated; g means gram or grams; mg means milligram or milligrams; ng means nanogram or nanograms; pg means picogram or picograms; cm means centimeter or centimeters; mm means millimeter or millimeters; L means liter or liters; L means microliter or microliters; $m/o$ means mole percent, and equals 100 times the number of moles of the constituent designated in a composition divided by the total number of moles in the composition; $v/v$ means percent by volume; $w/v$ means weight per unit of volume, and is in terms of g/L; M means molar and equals the number of gram moles of a solute in one liter of a solution; $\mu M$ means micromolar and equals the number of microgram moles in one liter of a solution; mM means millimolar and equals the number of milligram moles of a solute in one liter of a solution; N means normal, and equals the number of gram equivalents of a solute in one liter of solution; and $\mu N$ means micronormal and equals the number of microgram equivalents of a solute in one liter of solution. All temperatures are in C°, unless otherwise indicated.

Example 1 describes the recovery of intrinsic factor from pig duodenum, and the method of the invention for purifying the intrinsic factor. The following solutions were used in carrying out Example 1.

"PBS Buffer", a solution in deionized water, pH 7.4, containing 14.6 g/L $K_2HPO_4$, 2.18 g/L $KH_2PO_4$, and 9.0 g/L NaCl.

"GSS Solution", a solution in deionized water, pH 9 to 10, containing 7.52 g/L glycine, 34.2 g/L sucrose and 59.0 g/L NaCl.

EXAMPLE 1

About 40 pig duodenum were harvested, and placed on ice. They were kept on ice until the steps described below were carried out; all liquids used in cleaning and preparation of the duodenum were ice cold (temperature not higher than about 8°) and were kept ice cold as much as possible. The duodenum were cut lengthwise washed with deionized water and placed in an ice cold saline solution which contained 8.77 g NaCl per L. The strips were then minced with scissors, and placed in a 4 L Waring blender to which 500 mL ice cold PBS buffer and ice cold deionized water to bring to 2 L the volume of the materials in the blender were added. The contents were blended at low speed for 1 minute, transferred to a larger container, and diluted to a volume of 3 L with ice cold deionized water. The contents of the larger container were stirred for about 90 minutes; 30 minutes after the stirring started, they were acidified with 60 percent perchloric acid to pH 1.0 to 1.5. During the final hour of stirring the pH of the contents of the larger vessel was checked from time to time and more 60 percent perchloric acid was added, as necessary, to maintain the pH in the indicated range. The contents of the larger vessel were then transferred to 1 L centrifuge tubes and centrifuged at 4800 rpm until the solids were pelleted (about 30 minutes). The supernatant liquid was decanted into a single container; its volume was ascertained (about 2.4 L); and $K_2HPO_4$ and 5N KOH solution in deionized water were added until the solution contained 0.05 g per L of the former and had a pH in the range of 6.5 to 7.5. The solution stood for about 16 hours at 4° after which a precipitate had formed. The supernatant was decanted from the solids; a 2% $v/v$ addition of colloidal silica was made and the mixture stirred for 30 minutes; and the supernatant was centrifuged for 45 minutes at about 5000 rpm. The supernatant was decanted from the solids and was filtered through celite to remove colloids. The filtrate was a relatively impure solution of intrinsic factor which had been found by prior analytical work to contain an amount of R-protein that would bind to about 1 $\mu g$ cobinamide per mL of filtrate. Light was excluded from the filtrate; an addition of cobinamide amounting to 1 $\mu g$ per mL filtrate was made; and the filtrate and cobinamide were stirred in the dark for about 17 hours at a temperature of 2° to 8°. An addition of about 50 mL of an intrinsic factor affinity resin was made about 30 minutes after the cobinamide addition. The affinity resin was one which had a B 12 derivative ligated to agarose. After stirring was discontinued the crude mixture was filtered through a coarse scintered glass funnel and the remaining gel was washed with successive volumes of GSS solution (500 ml), PBS (500 ml), 4M NaCl (500 ml) and finally 1 L of PBS. The washed gel, containing bound intrinsic factor, was loaded into a glass chromatography column.

Figure 2:
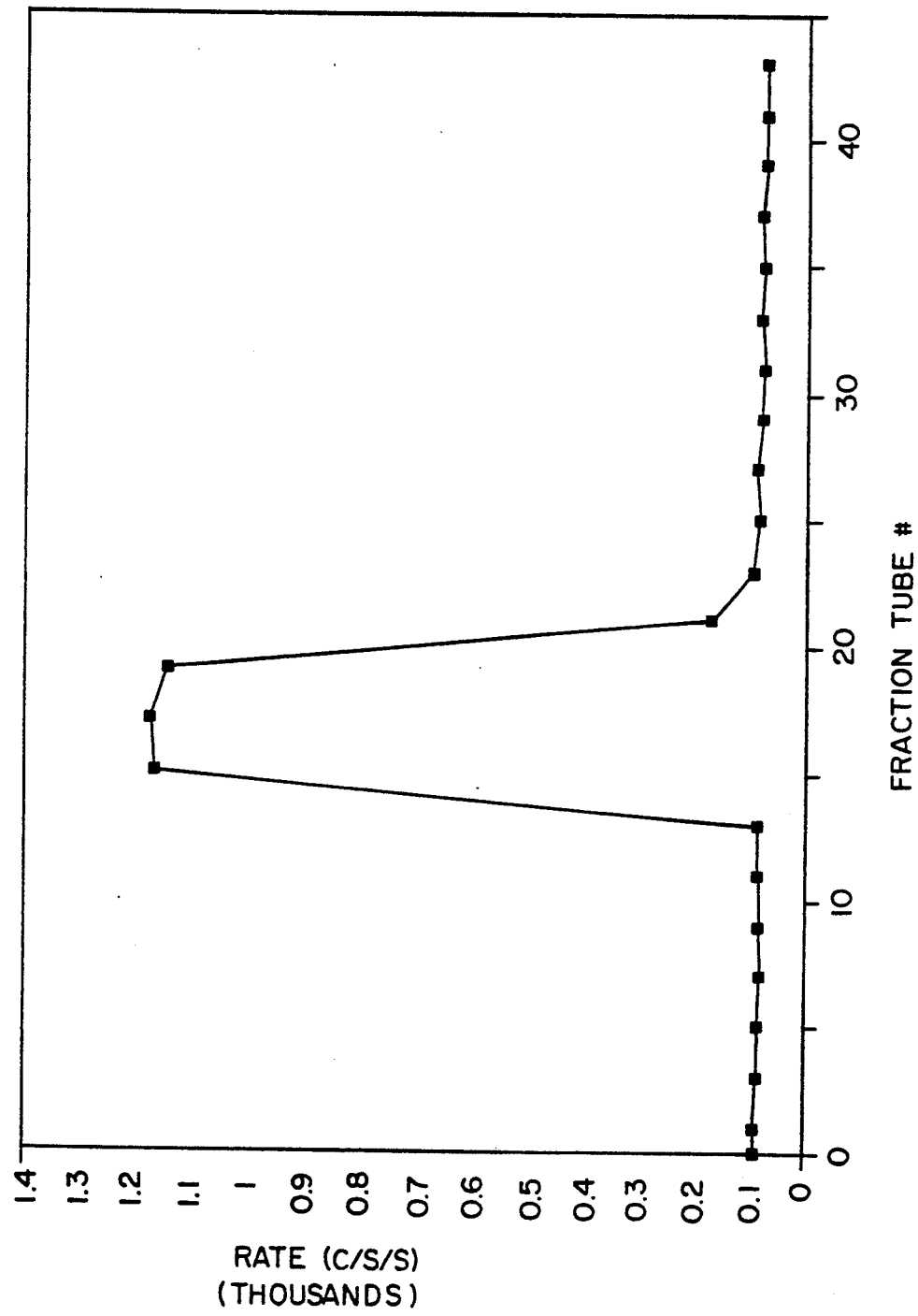
FIG. 2 is a plot showing the elution of purified hog intrinsic factor from the affinity gel column.

The intrinsic factor was eluted with 3.8 M Guanidine-HCl as shown in FIG. 2. The initial intrinsic factor fraction eluted from the column contained the intrinsic factor selected for use in the assays of this invention; later fractions yielded assays with lesser performance. The intrinsic factor in the desired fractions was tested for the presence of R proteins, FIG. 3, which bind many porphyrin ring containing compounds (i.e. cobinamides) including but not limited to cobalamins. Once the intrinsic factor was tested (by radioassay using B12 cobalt 57) to contain less than 0.004 percent cross-reactivity with cobinamides, the intrinsic factor was exhaustively dialyzed with several changes of deionized water. The first fraction, affinity purified in this manner ("Purified Intrinsic Factor"), has been found to contain proteins of which at least 95% bind cobalamins. Less than about 95 percent functional purity was found to yield assays with impaired sensitivity.

Figure 3:
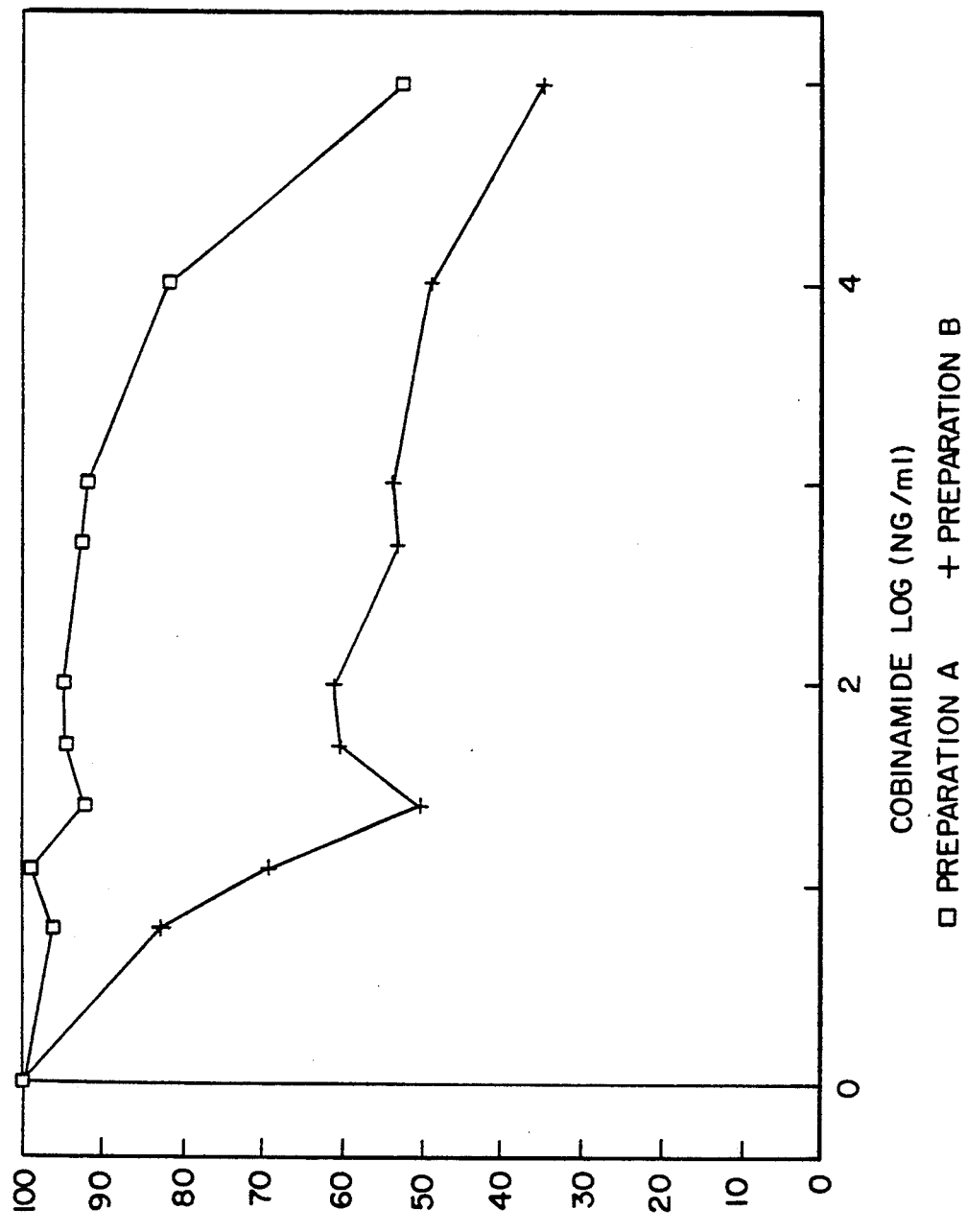
FIG. 3 is a plot showing the sensitivity of intrinsic factor preparations to increasing concentrations of cobinamide dicyanide. Plot A is intrinsic factor (IF) purified as in Example 1, plots B&C are IF prepared as in Example 5.

For the purposes of comparison, but not in accord with the instant invention, the procedure of Example 1 was repeated, with the exception that the colloidal silica and cobinamide additions were not made prior to the recovery of the purified intrinsic factor by affinity chromatography. The relative purity of this preparation, B, and the purified intrinsic factor of Example 1, A, was tested by determining the cobinamide-sensitive fraction of the total corrin binding capacity in each preparation, as shown in FIG. 3. The amount of $^{57}Co$—B12 binding activity displaced by increasing amounts of cobinamide added to a sample counting $^{57}Co$—B12, buffer and either intrinsic factor preparation A or B, is an indication of the amount of non-intrinsic factor (R-protein) corrin binding protein containment present in preparation A or B.

Figure 5:
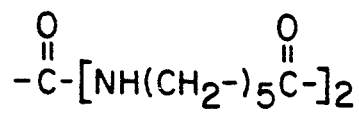
FIG. 5 is a formula showing a chemical moiety by which purified intrinsic factor is linked to microparticles in a conjugate produced as described in Example 2 hereof.
Figure 6:
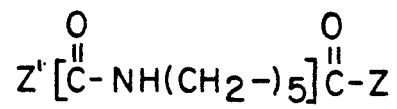
FIG. 6 is a formula showing the structure of the 23 atom linker, where n=2, Z has the structure of FIG. 7 and Z' the structure of FIG. 8, which can be used to produce a conjugate according to the instant invention.
Figure 7:
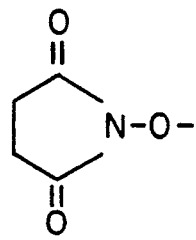
FIG. 7 is a formula showing the structure of preferred end groups in the family of compounds of FIG. 9.
Figure 8:
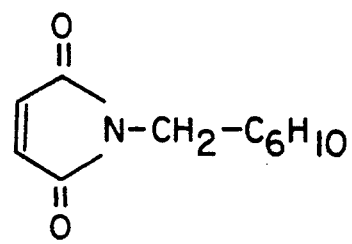
FIG. 8 is a formula showing another end group structure in compounds which can be used to produce conjugates of the instant invention.

Example 2 describes the production of a conjugate of treated microparticles and Purified Intrinsic Factor connected to one another by groups having the structure of FIG. 5 of the attached drawings. The treatment of the microparticles and the production of a 23 atom linker (an N-hydroxysuccinimidyldicaproamidocyclohexylmethylmaleimide) which was used in producing the conjugate are described below as an introduction to the example. The 23 atom linker has the structure of FIG. 6 of the drawings, where n is 2, Z has the structure of FIG. 7, and Z' has the structure of FIG. 8 where $C_6H_{10}$ is 1,4-cyclohexylene. The production of a 17 atom linker intermediate (an N-hydroxysuccinimidylcaproamidocyclohexylmethylmaleimide) is also described; the 17 atom linker has the structure of FIG. 6 of the drawings, where n is 1, and Z, Z' and $C_6H_{10}$ have the meanings stated in the preceding sentence. The above linkers are further described and claimed in co-pending, co-owned patent application U.S. Ser. No. 07/534,381 filed on Jun. 6, 1990 and hereby incorporated by reference.

TREATMENT OF MICROPARTICLES

A 0.5 g portion of a resin which is commercially available under the trade designation BIORAD BIO-REX MSX 501 (D) was washed several times with deionized water. A 1 mL portion of amino microparticles (SERADYNE, average diameter 0.26 M; average parking area 390 angstroms$^2$ per amine group) and about 1 mL deionized water were then mixed with the resin, and the mixture was rotated for one hour at room temperature. The resin was allowed to settle, and the microparticles were decanted. Another 1 mL addition of deionized water was made to the resin and, after mixing, the microparticles were again decanted. The water rinse, mix and decant steps were carried out twice more, and deionized water was added to the decanted microparticles to bring the microparticle solids content to 7.5 percent ("Treated Microparticles").

(A) Preparation of N-hydroxysuccinimidylcaproamidocyclohexylmethylmaleimide

An N-hydroxysuccinimidylcaproamidocyclohexylmethylmaleimide, (structure of FIG. 6 where n is 1 and Z, Z', and $C_6H_{10}$ have the meanings stated above) was first produced from a solution of 100 mg N-(4-carboxycyclohexylmethyl) maleimide in dry dimethylformamide, 39.23 mg 6-aminocaproic acid, 67.8 mg dicyclohexylcarbodiimide and 37.8 mg N-hydroxysuccinimide. The N-(4-carboxycyclohexylmethyl) maleimide was produced from trans-4-(aminomethyl)-cyclohexanecarboxylic acid (Aldrich Chemical Co.) by the method of Yoshitake et al. J.Biochem., 101:395–399(1979)). A nitrogen atmosphere was established in a flask above the N-(4carboxycyclohexylmethyl) maleimide solution, and the 6-aminocaproic acid was added to the flask. The reaction mixture was then stirred under nitrogen at room temperature of about 22° for 16 hours, after which time the dicyclohexylcarbodiimide and the N-hydroxysuccinimide were added to the flask. Stirring at room temperature was continued for an additional 6 hours, after which time dicyclohexylurea which had precipitated was removed from the reaction mixture by filtration, and the dimethylformamide was evaporated under reduced pressure from the filtrate. A tacky solid which remained was purified by flash chromatography on silica gel 5 (5$^v$/$_v$, methanol in chloroform), yielding 71 mg N-hydroxysuccinimidylcaproa-midocyclohexylmethylmaleimide, a white solid which has the indicated formula.

(B) Preparation of N-hydroxysuccinimidyldicaproamidocyclohexylmethylmaleimide An N-hydroxysuccinimidyldicaproamidocyclohexylmethylmaleimide (structure of FIG. 6 where n is 1 and Z, Z' and $C_6H_{10}$ have the meanings stated above) was then produced from a 10 solution of 100 mg N-hydroxysuccinimidylcaproamidocyclohexylmethylmaleimide in 1 ml dry dimethylformamide, 29.3 mg 6-aminocaproic acid and 50.7 mg dicyclohexylcarbodiimide. A nitrogen atmosphere was established in a flask above the N-hydroxysuccinimidylcaproamidocyclohexylmethylmaleimide solution, and the 6-aminocaproic acid was added to the flask. The reaction mixture was then stirred under nitrogen at room temperature of about 22° for 16 hours, 15 after which time the dicyclohexylcarbodiimide was added to the flask. Stirring at room temperature was continued for an additional 6 hours, after which time dicyclohexylurea which had precipitated was removed from the reaction mixture by filtration, and the dimethylformamide was evaporated under reduced pressure from the filtrate. A tacky solid which remained was purified by flash chromatography on silica gel (10 $^v$/$_v$, methanol in chloroform), yielding 60 mg of the N-hydroxysuccinimidyldicaproamidocyclohexylmethylmaleimide, which has the indicated formula.

EXAMPLE 2

Microparticle Functionalization

A microparticle/intrinsic factor conjugate was produced by combining Treated 25 Microparticles, 700 L Purified Intrinsic Factor solution which contained 38 g per mL intrinsic factor and 80 g of the 23 atom heterobifunctional linker produced as described above in 17.5 mM triethanolamine butter (pH8.0) to produce 1 mL of a solution which contained 0.6 percent of the microparticles. The solution which resulted was mixed for 2 hours in the dark at room temperature of about 22°. After incubation, the particles were pelleted and washed several times in mild detergent /50 mM TRIS buffer solution, homogenized to ensure uniform particle size distribution, and diluted to the desired concentration ("Intrinsic Factor-Microparticle Conjugate").

Figure 9:
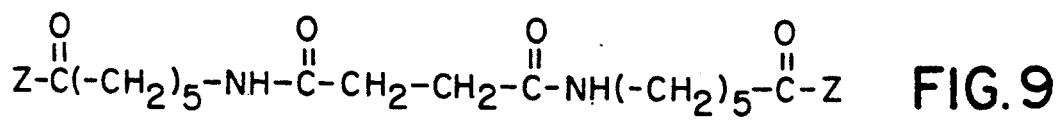
FIG. 9 is a formula showing the structure of a family of compounds that can be used to produce a conjugate of alkaline phosphatase and "B12 AMINE", a B12 derivative defined herein; the conjugate can be used in carrying out an enzyme assay for cobalamins.
Figure 10:
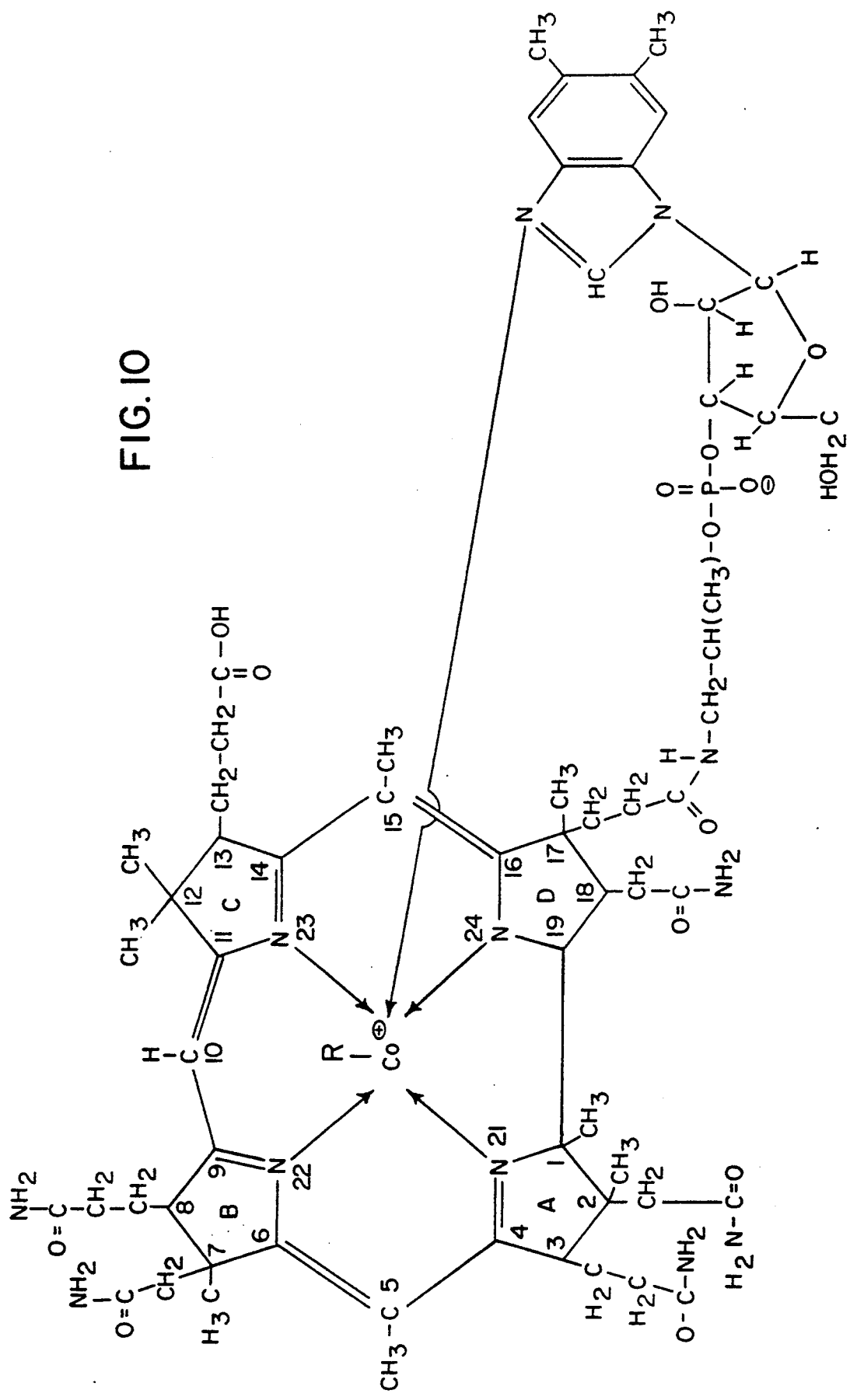
FIG. 10 is a formula showing the structure of a "red fraction" whose preparation is described herein, and is named "CARBOXYLATED B-12".

Examples 3 and 4 describe the derivation of a standard curve showing signal as a function of cyanocobalamin concentration in standard solutions when enzyme linked B12 assays were performed on a fully automated machine (ABBOTT IMx ® analyzer) and the use of the standard curve to assay unknown samples for cobalamin. The Intrinsic Factor-Microparticle Conjugate is used in the enzyme assay, as is a second conjugate in which a chemical moiety from an 18 atom homobifunctional linker binds "BI2 AMINE" to alkaline phosphatase. The production of the 18 atom homobifunctional linker, which has the structure of FIG. 9 of the attached drawings, the production of the B12 AMINE, a compound having the structure of FIG. 10 of the attached drawings, except that the substituent attached to the 13 carbon in the C ring has the structure

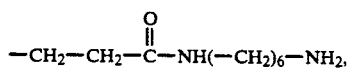

and the use of the 18 atom homobifunctional linker to bind alkaline phosphatase to B12 AMINE, are described below, as an introduction to Examples 3 and 4.

PRODUCTION OF B12 AMINE

The B12 AMINE was produced by acid hydrolyzing 2.2 g cyanocobalamin, isolating the monocarboxylic acids which were produced, and coupling the acids to 1,6-diamino hexane.

Production and isolation of Monocarboxylic acids

The cyanocobalamin was added to 300 mL 0.8 M phosphoric acid and heated for six hours at 70° in the dark under a nitrogen blanket. The reaction mixture was applied to a washed ion exchange resin packed in a column; unbound derivatives were eluted; and the bound B12 acids were eluted with methanol and concentrated by rotary evaporation. The ion exchange resin used is one that is available under the trade designation AMBERLITE XAD-2. The individual B12 acids were then separated on a DE-52 Cellulose column, washed with NAOH, HCl and NaOAc, and equilibrated to pH 5.0 with deionized water. The sample was then added to a 4×75 cm column, and slowly eluted. After two days, a single red band containing unreactive corinoid was removed with distilled water. The B12 monoacids were eluted with 0.05 percent acetic acid. Three peaks were eluted in 36 hours. Each band was collected and concentrated by rotary evaporation. Fractions which contained red material were pooled, while orange-yellow fractions were discarded. A radioassay was used to test the red fractions for reactivity. Mass spectroscopy, C13 NMR and HPLC were used to characterize the red fractions; they were found to have the structure of FIG. 10 of the attached drawings ("MONOCARBOXYLATED B12"); that is, they were carboxylated in position 13 on the C ring.

Production of B12 AMINE

The B12 AMINE was then produced from 63 mg MONOCARBOXYLATED B12, 0.2554 g 1,6-hexyl diamine and 88.8 mg 1-ethyl-3-(3-dimethylaminopropyl)-carbodiimide ("EDAC"). The MONOCARBOXYLATED B12 and the 1,6-hexyl diamine were dissolved in 13 mL distilled water; the pH of the solution was adjusted to 6.0 with 1N HCl; the EDAC was added; and the reaction mixture was stirred for about 16 hours under a nitrogen blanket [Tetsuo Toraya, *J. Biol. Chem.*, 255; 3520-3525 (1980)]. The reaction mixture was concentrated by rotary evaporation and purified by HPLC [Tetsuo Toraya, *Biochem.*, 18:417-426 (1979)]. The B12 AMINE was purified on a C- 18 (Magnum 9) column using a solvent system composed of 20 $v/v$ methanol and 80 $v/v$ 1 percent aqueous acetic acid at an initial flow rate of 4 ml per minute; after 80 minutes the flow rate was increased to 6 ml per minute. The product was identified as B12 AMINE.

SYNTHESIS OF THE 18 ATOM HOMOBIFUNCTIONAL LINKER

(A) Synthesis of ester intermediate

Figure 11:
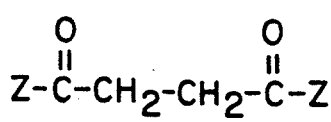
FIG. 11 is a formula for a family of active esters, which are intermediate intermediates a procedure described herein for the production of compounds having the structure of FIG. 9.

A disuccinimidyl ester intermediate was first produced from 8.16 g N-hydroxysuccinimide dissolved in 200 mL dimethylformamide, 7.17 g triethylamine and 5.0 g succinyl chloride. The triethylamine was added to the dimethylformamide solution under a nitrogen blanket. Stirring was commenced and was continued while the succinyl chloride was added slowly and for eight hours after the addition was complete. The precipitate which formed was separated from the reaction mixture by filtration, and was dried under high vacuum, yielding crude product which was triturated with 50 mL chloroform and dried in an argon stream under high vacuum, yielding 0.52 g pure white powder which was identified as the disuccinimidyl ester intermediate, a compound which has the structure of FIG. 11 of the attached drawings where Z has the structure of FIG. 7.

(B) Synthesis of linker

The 18 atom homobifunctional linker was then synthesized from 5.0 g disuccinimidyl ester intermediate dissolved in 150 ml dry dimethylformamide, 4.20 g 6-aminocaproic acid and 6.93 g dicyclohexylcarbodiimide. The 6-aminocaproic acid was added to the dimethylformamide solution, and the resulting reaction mixture was stirred under a nitrogen blanket for three hours at room temperature of about 22°. The dicyclohexylcarbodiimide was then added, and the reaction mixture was stirred under a nitrogen blanket for about 16 hours at room temperature. Dicyclohexyl urea precipitate which had formed was then separated from the reaction mixture by filtration, and dimethylformamide was evaporated from the filtrate under reduced pressure. Trituration with ether followed by drying under high vacuum yielded 7.94 g 18 atom homobifunctional linker.

Production of the B12:Alkaline Phosphatase Conjugate

The conjugate was prepared from:
(1) 0.173 mL 0.82 mM B12 AMINE solution in 50 $v/v$ dimethyl-formamide and dimethylsulfoxide,
(2) 0.142 mL 1.88 mM 18 atom homobifunctional linker solution in 50 $v/v$ dimethylformamide and dimethylsulfoxide,
(3) 1.0 mL alkaline phosphatase (Boehringer Mannheim; 10 mg/ml) that had been dialyzed in 50 mM potassium phosphate buffer (pH 7.4) containing 0.1 mM zinc chloride, and
(4) 0.0749 mL 50 $v/v$ dimethylformamide and dimethylsulfoxide.

Figure 12:
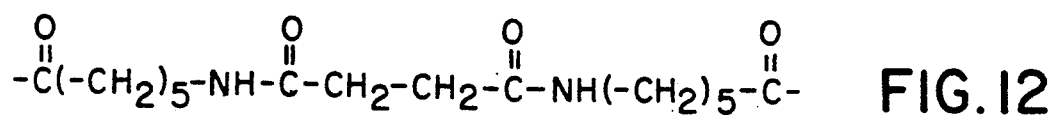
FIG. 12 is a formula showing the structure of a group by which B12 molecules are linked to alkaline phosphatase molecules in a B12/alkaline phosphatase conjugate produced as described herein.

The B12 AMINE solution, the 18 atom homobifunctional linker solution and the 50 dimethylformamide and dimethylsulfoxide were mixed in a glass vial and allowed to react at room temperature of about 22° for 30 minutes. The reaction mixture was then added to the dialyzed alkaline phosphatase, mixed gently, and allowed to stand for about 20 hours at 4°. The reaction mixture was separated on Sephadex G 50-100 (1.2×44 cm) using 50 mM tris(hydroxymethyl)-aminomethane ("TRIS"; pH 7.4) in deionized water which additionally contained 1.0 mg mole per liter magnesium chloride and 0.10 mg mole per liter zinc chloride. The appropriate fractions were pooled and dialyzed against 1000 ml TRIS (pH 7.4) in deionized water which additionally contained 1.0 mg mole per liter magnesium chloride and 0.10 mg mole per liter zinc chloride. The product was a B12/alkaline phosphatase conjugate in which B12 molecules were linked to alkaline phosphatase molecules by groups which had the structure of FIG. 12 of the attached drawings, the Z groups of FIG. 2 having been displaced during preparation of the conjugate. The B12/alkaline phosphatase conjugate was then diluted to a desired concentration to produce an "Enzyme-B12 Conjugate Working Solution".

The Enzyme-B12 Conjugate Working Solution, the Intrinsic Factor-Microparticle Working Conjugate and a "Working Substrate Indicator" were used in carrying out the procedures of Examples 3 and 4. The Working Substrate Indicator was a 100 mM solution of 2-amino-2methyl-1 -propanol (pH 10.3) which also contained I mg mole per L MgCl214 mg moles per L tetramisole, ·1.2 mg moles per L 4-methylumbelliferone-phosphate ("MUP") and 0.1 percent NaN3.

ASSAY PROTOCOL USED IN PERFORMING ENZYME LINKED B12 ASSAY

A standard or a serum sample was denatured at 34° for 8 minutes by adding cobinamide, a thiol reagent such as α-monothioglycerol and NAOH until the standard or sample contained 0.3 g equivalent per L sodium hydroxide (the purpose of this step was to dissociate B12 from serum binding proteins). The denatured solution was then neutralized with the Intrinsic Factor-Microparticle Working Conjugate, and the neutralized composition was incubated for 15 minutes at room temperature. The incubated composition was then deposited on a separation material surface, which was an IMx ® disposable reaction cell sold by Abbott Laboratories, North Chicago, Ill.; B12 bound to intrinsic factor conjugated to the microparticles was retained on the separation material surface, while B12 that was not so bound could be washed away. The separation material surface was then washed with a 50 mM TRIS (pH 7.4) solution in deionized water to free it of unbound B12. A 50 L portion of the Enzyme-B12 Conjugate Working Solution was added to the separation material surface to bind free intrinsic factor sites. The separation material surface was again washed with the 50 mM TRIS (pH 7.4) solution in deionized water, after which a 50 μL portion of the Working Substrate Indicator was added and the separation material surface was excited with radiation having a wavelength of 362 nm. MUP is hydrolyzed by alkaline phosphatase, releasing 4-methylumbelliferone, which fluoresces when excited by radiation having a wavelength of 362 nm, emitting radiation having a wavelength of 448 nm. The reading given by the IMx ® instrument was the initial intensity per unit of time of the emission at a wavelength of 448 nm when the alkaline phosphatase substrate indicator was added to the separation material surface.

EXAMPLE 3

Figure 13:
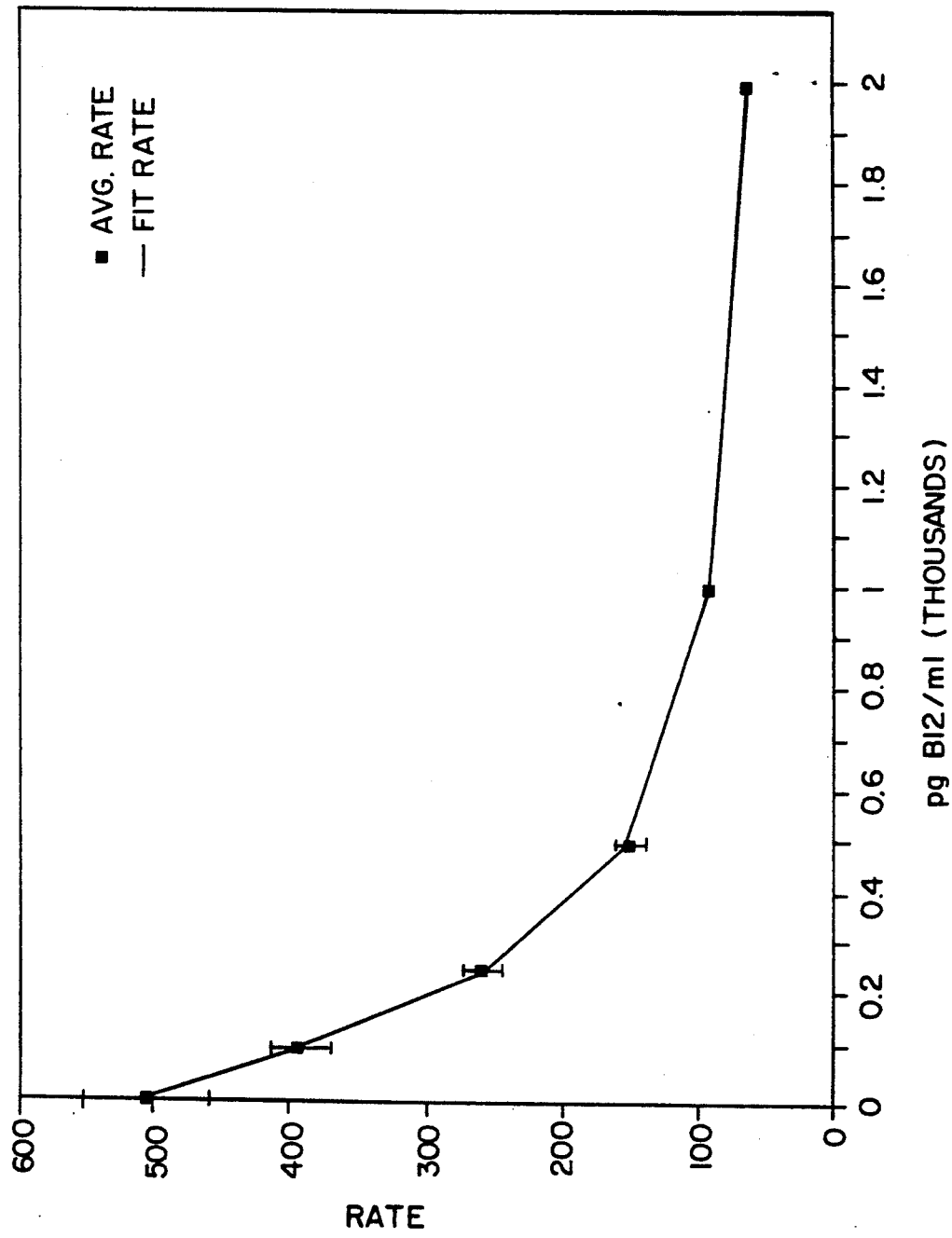
FIG. 13 is a curve showing instrument readings as a function of cyanocobalamin concentration in standard solutions prepared as described herein.

The foregoing protocol was used to determine signal as a function of cyanocobalamin concentration in standards prepared by diluting USP cyanocobalamin in 50 mM TRIS solution (pH7.4) in deionized water which also contained 1 percent bovine serum albumen, 0.2 percent NaN3, 100 mg moles per L of NaCl, 1.0 mg mole per L of NaCl and 0.1 mg mole per L ZnCl2. The standards contained 0, 100, 250, 500, 1000, and 2000 pg/ml cyanocobalamin. The IMx ® instrument readings from the standard samples gave data for a curve showing readings as a function of B12 content. This curve is FIG. 13 of the attached drawings.

EXAMPLE 4

Figure 14:
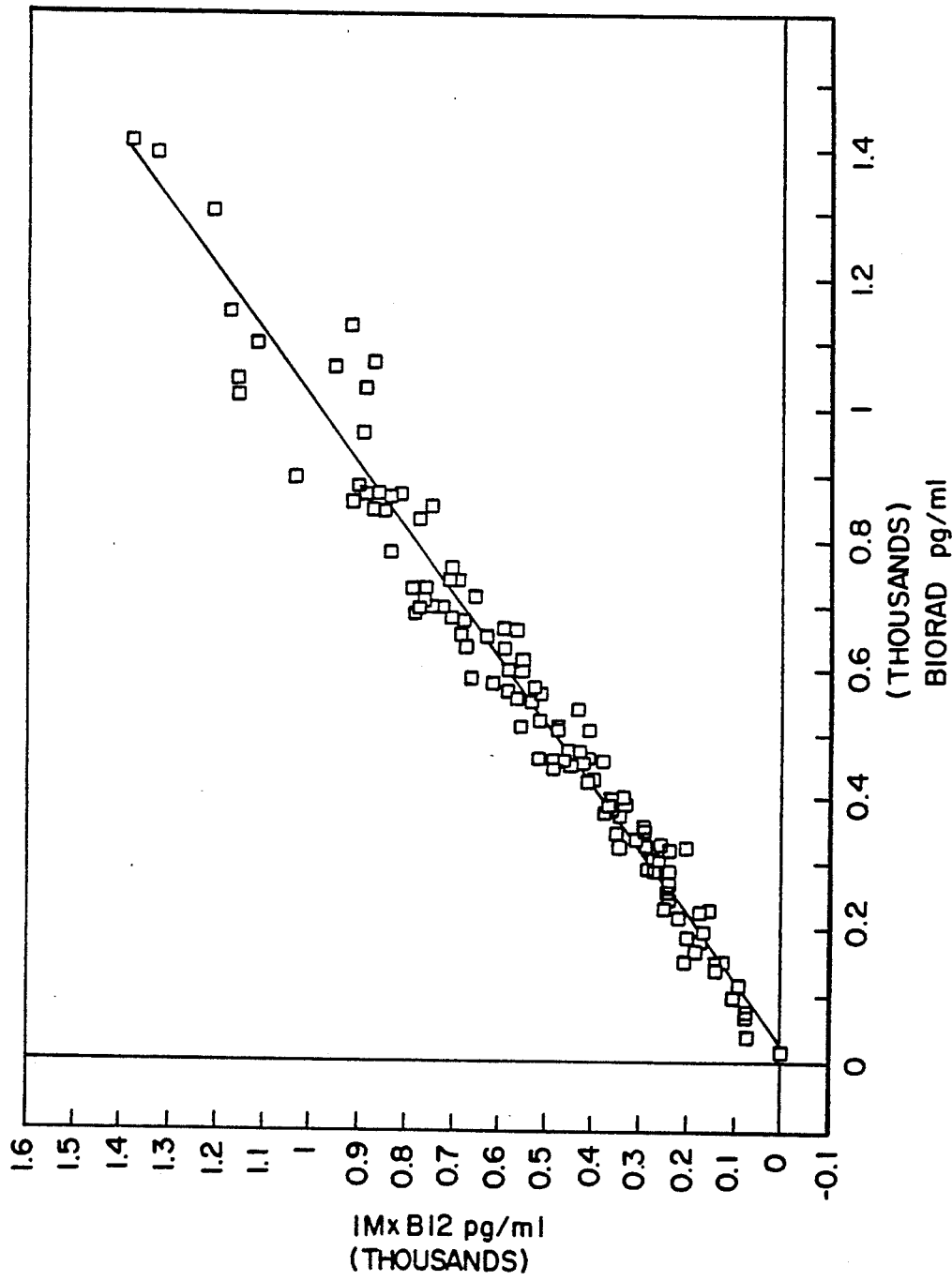
FIG. 14 is a plot of enzyme assay determinations of B12 against "BIO-RAD QUANTIPHASE" determinations of B12 in the same samples.

The foregoing protocol was used to determine the signal from various patient samples. It has been found that the assay is capable of detecting less than 60 pg per mL B12, based on a calculation using two times the standard deviation of multiple runs of the zero standard. Patient serum samples (n=76) were assayed as described above, and in radioassay apparatus that is commercially available under the designation BIORAD, Quantaphase TM radioassay. The correlation curve, FIG. 14 of the attached drawings, was calculated from the data from the two test methods; the slope of the curve was found to be 1.10, while the correlation coefficient (R) was 0.99.

EXAMPLE 5

Figure 4:
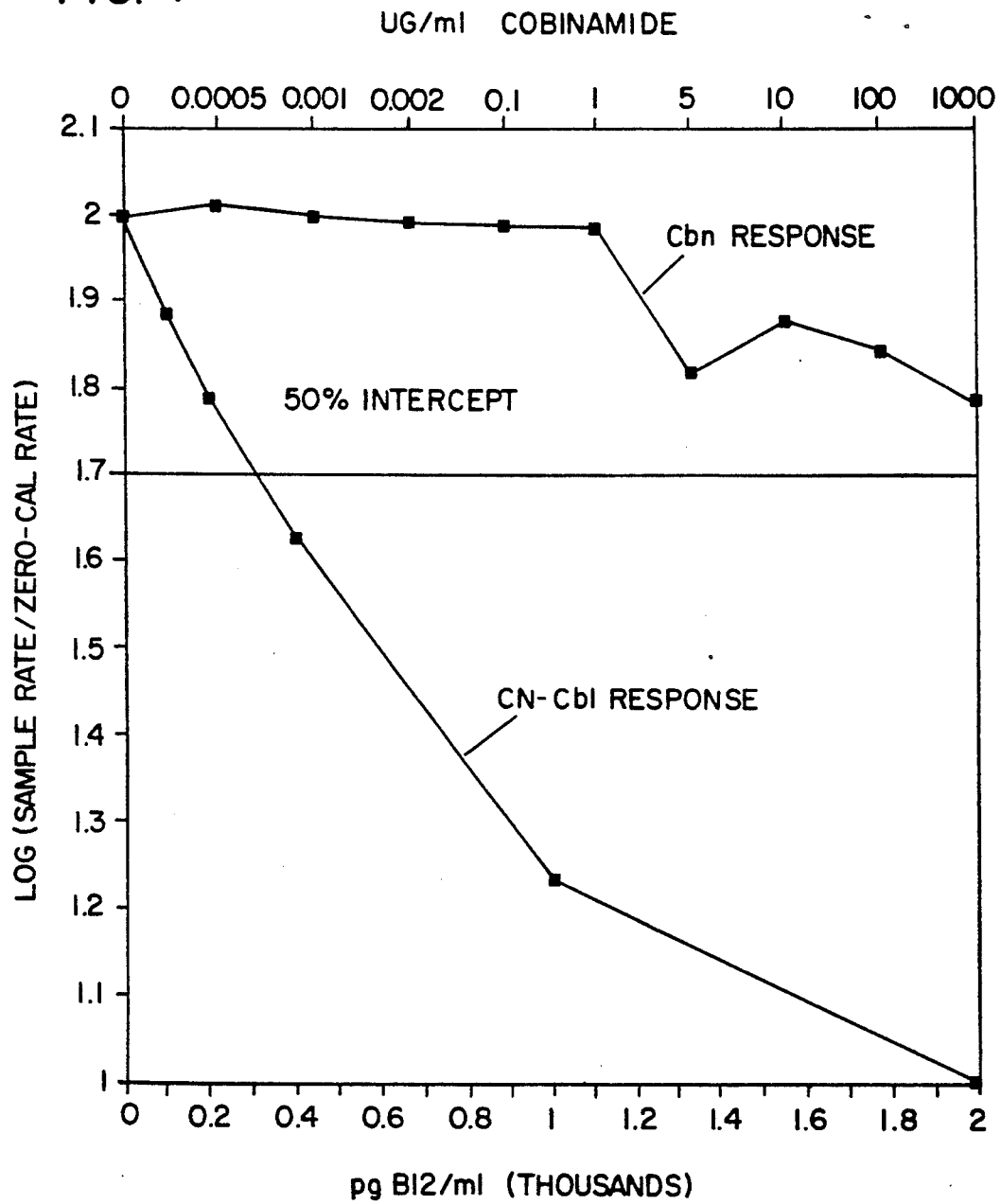
FIG. 4 is a plot showing the sensitivity of the B12 assay described in Example 5 to increasing concentrations of cobinamide dicyanide.

The foregoing protocol of Example 3 was used to determine the sensitivity of the assay, using intrinsic factor purified as stated in this invention, to interferences from the physiologically-inactive vitamin B12 analog, cobinamine. Increasing amounts of cobinamide were added to the zero standard. A curve was plotted showing the degree of displacement of the zero standard with increasing amounts of added cobinamide, vs. a calibration curve generated using standards without cobinamide. These curves are shown in FIG. 4. By dividing the amount of vitamin B12 required to displace the zero standard 50%, by the amount of cobinamide added to achieve 50% displacement of the zero standard, the total cross-reactivity of the assay with cobinamide was calculated to be less than 0.004%.

We claim:

1. A conjugate of microparticles and intrinsic factor purified by separation of R-proteins therefrom to such an extent that the purified material contains less than 0.004 percent cross reactivity with cobinamides.

2. A conjugate of microparticles and intrinsic factor as claimed in claim 1 wherein at least 95 percent of the proteins bind cobalamins.

3. A kit for conducting an assay for cobalamins, said kit comprising a conjugate of microparticles and intrinsic factor purified by separation of R-proteins therefrom to such an extent that the purified material contains less than 0.004 percent cross reactivity with cobinamides, a conjugate of an enzyme and a specific binding member for the purified intrinsic factor and a substrate indicator which reacts with the enzyme to produce a signal or to produce a reaction product which can be caused to produce a signal.

4. A kit as claimed in claim 3 wherein the enzyme is alkaline phosphatase and the indicator is MUP.

5. A kit as claimed in claim 4 wherein the specific binding member is B12 AMINE.

6. A method for conducting an assay for cobalamins, said method comprising denaturing a test sample, adding to the denatured test sample a conjugate of microparticles and intrinsic factor purified by separation of R-proteins therefrom to such an extent that the purified material contains less than 0.004 percent cross reactivity with cobinamides, incubating the denatured test sample containing the conjugate, depositing the incubated composition on a separation material which retains the intrinsic factor/microparticle conjugate, washing the separation material surface to remove unbound B12, adding a conjugate of an enzyme and a specific binding member for the purified intrinsic factor to the separation material to bind free intrinsic factor sites, washing the separation material, adding a substrate indicator which reacts with the enzyme to produce a signal or to produce a reaction product which can be caused to produce a signal, and measuring the signal produced by reaction between the enzyme and the indicator or causing the product of the reaction between the enzyme and the indicator to produce a signal and measuring the signal.

* * * * *